United States Patent [19]
Palazzotto et al.

[11] Patent Number: 6,017,660
[45] Date of Patent: *Jan. 25, 2000

[54] INKS CONTAINING A TERNARY PHOTOINITIATOR SYSTEM AND IMAGE GRAPHICS PREPARED USING SAME

[75] Inventors: Michael C. Palazzotto; F. Andrew Ubel, III; Joel D. Oxman; M. Zaki Ali, all of St. Paul, Minn.

[73] Assignee: 3M Innovative Properties Company, St. Paul, Minn.

[ * ] Notice: This patent is subject to a terminal disclaimer.

[21] Appl. No.: 09/094,184

[22] Filed: Jun. 9, 1998

Related U.S. Application Data

[63] Continuation of application No. 08/695,566, Aug. 12, 1996, abandoned, which is a continuation of application No. 08/365,494, Dec. 28, 1994, Pat. No. 5,545,676, which is a continuation of application No. 07/840,880, Feb. 25, 1992, abandoned, which is a continuation of application No. 07/034,065, Apr. 2, 1987, abandoned.

[51] Int. Cl.[7] .............................. G03C 1/73; C09D 11/10; B32B 27/16; G03F 7/029
[52] U.S. Cl. ........................... 430/17; 430/18; 430/281.1; 430/915; 430/916; 106/20 B; 522/14; 522/15; 522/75; 522/81; 522/16; 522/25; 522/26; 522/28; 522/78; 522/85
[58] Field of Search .................................. 522/15, 14, 25, 522/26, 75, 81, 16, 28, 78, 85; 430/270.1, 270.11, 281.1, 915, 919, 916, 17, 18; 523/160; 106/20 B

[56] References Cited

U.S. PATENT DOCUMENTS

| | | | |
|---|---|---|---|
| 3,427,161 | 2/1969 | Urbain | 96/35.1 |
| 3,479,185 | 11/1969 | Chambers | 96/84 |
| 3,729,313 | 4/1973 | Smith | 96/27 R |
| 3,741,769 | 6/1973 | Smith | 96/35.1 |
| 3,756,827 | 9/1973 | Chang | 96/86 P |
| 3,759,807 | 9/1973 | Osborn | 204/159.23 |
| 3,778,274 | 12/1973 | Inoue et al. | 96/91 |
| 3,808,006 | 4/1974 | Smith | 96/88 |
| 3,933,682 | 1/1976 | Bean | 522/26 |
| 4,011,063 | 3/1977 | Johnston | 51/295 |
| 4,047,903 | 9/1977 | Hesse et al. | 51/298 |
| 4,069,054 | 1/1978 | Smith | 96/115 |
| 4,071,424 | 1/1978 | Dart | 204/159.15 |
| 4,126,428 | 11/1978 | Rude | 51/295 |
| 4,156,035 | 5/1979 | Tsao et al. | 427/44 |
| 4,228,232 | 10/1980 | Rosseau | 430/271 |
| 4,240,807 | 12/1980 | Kronzer | 51/295 |
| 4,250,053 | 2/1981 | Smith | 252/426 |
| 4,284,551 | 8/1981 | Argentar | 523/116 |
| 4,298,356 | 11/1981 | Teschner et al. | 51/297 |
| 4,351,708 | 9/1982 | Berner et al. | 204/159.23 |
| 4,394,403 | 7/1983 | Smith | 427/42 |
| 4,407,984 | 10/1983 | Ratcliffe | 522/37 |
| 4,428,807 | 1/1984 | Lee et al. | 204/159.14 |
| 4,457,766 | 7/1984 | Caul | 51/298 |
| 4,476,215 | 10/1984 | Kausch | 522/25 |
| 4,503,169 | 3/1985 | Randklev | 523/117 |
| 4,507,382 | 3/1985 | Rousseau | 522/14 |
| 4,535,052 | 8/1985 | Anderson et al. | 430/277 |
| 4,547,204 | 10/1985 | Caul | 51/298 |
| 4,576,975 | 3/1986 | Reilly | 522/13 |
| 4,642,126 | 2/1987 | Zador et al. | 51/295 |
| 4,652,274 | 3/1987 | Boettcher et al. | 51/298 |
| 4,694,029 | 9/1987 | Land | 522/26 |
| 4,719,149 | 1/1988 | Aasen et al. | 522/28 |
| 4,735,632 | 4/1988 | Oxman et al. | 522/14 |
| 4,889,792 | 12/1989 | Palazzotto | 522/14 |
| 5,154,762 | 10/1992 | Mitra et al. | 523/116 |
| 5,545,676 | 8/1996 | Palazzotto et al. | 522/15 |

FOREIGN PATENT DOCUMENTS

| | | |
|---|---|---|
| 150952 | 8/1985 | European Pat. Off. . |
| 1304112 | 1/1973 | United Kingdom . |
| 2029428 | 3/1980 | United Kingdom . |

OTHER PUBLICATIONS

Baumann, H., U. Oertel and H. J. Timpe, Euro. Polm. J., 22(4), 313 (Apr. 3, 1986).
Baumann, H., B. Strehmel, H. J. Timpe and U. Lammel, J. Prakt. Chem. 326, (3)415–425 (1984).
Bull. Chem. Soc. Japan, 42, 2924–2930 (1969).
Chem. Abs. 95:225704U. (1995).
Crivello, J. V., Lee, J. L. and Conlon, D. A., J. Rad. Curing, 10, (1), 6–13 (Jan. 1983).
Gatechair, L. R. and Pappas, S. P., Organic Coatings and Applied Polymer Science Proceedings, 46, 701–707 (ACS, 183rd National Meeting, Las Vegas, Nevada, Mar. 29 1982).
Perkins, W. C., J. Rad. Curing, 8, (1), 1623 (Jan. 1981).
Mann, C. K. and Barnes, K. K., Electrochemical Reactions in Nonaqueous Systems (1970), Marcel Dekker, Inc., New York, pp. 8–9.
Timpe, H. J. and Baumann, H., Wiss. Z. Tech. Hochsch. Leunn–Merseberg, 26, 439 (1984).
Weinburg, N. L., Ed., Technique of Electroorganic Synthesis Part II Techniques of Chemistry, vol. V, p. 8, (1975) Part II.
Crivello, J. V. and Lam, J. K. w., Journal of Polymer Science: Polymer Letters Edition, 17, 759–764 (1979).
Brauer et al., J. Polym. Sci., 19, 311 (1956).
Chem, J. Polm. Sci.: Part A, 3, 1807 (1965).
Chaberek et al., J. Phys. Chem., 69, 641 (1965):id, 69, 647 (1965); id, 69, 2834 (1965).
Cohen et al., Chem. Rev., 73, 141 (1973).
Crivello et al., J. Polym. Sci. Polym. Chem., 16, 2441 (1979); id, 17, 1047 (1979); id, 17, 1059 (1979); id, 18, 1021 (1980).
Foreman et al., JACS, 102, 1170 (1980).
Guttenplan et al., JACS, 94, 4040 (1972).

(List continued on next page.)

*Primary Examiner*—Susan W. Berman
*Attorney, Agent, or Firm*—Dale A. Bjorkman

[57] ABSTRACT

Photocurable addition-polymerizable compositions containing a free-radically-polymerizable monomer and a photoinitiator system containing i) an arylidonium salt, ii) a sensitizing compound, and iii) an electron donor having an oxidation potential that is greater than zero and less than or equal to that of p-dimethyoxybenzene (1.32 volts vs. S.C.E.). The compositions cure rapidly and deeply under ultraviolet or visible light.

35 Claims, No Drawings

OTHER PUBLICATIONS

Ledweth, The Exiplex, 209 (1975).

Ledweth, J. Oil Col. Chem. Assoc., 59, 157 (1976); id, 61, 95 (1978).

Margerum et al., Photogr. Sci. Eng, 12, 177 (1968).

Margerum et al., J. Phys. Chem., 75, 3066 (1971).

Overberger et al., J. Polym. Sci., 40, 179 (1959).

Rust et al., Polym. Eng. Sci., 9, 40 (1969).

Williams et al., Polym. Eng. Sci., 23, 1022 (1983).

Yamese et al., Photogr. Sci. Eng., 17, 28 (1973); id 17, 268 (1973); id 18, 25 (1974); id 18, 647 (1974); and ID 19, 57 (1975).

Chemical Abstract #413484 of vol. 106, 1986.

Kosar, "Light Sensitve Systems", pp. 54–61, 165, John Wiley & Sons, NY.

Kosar, "Light Sensitive Systems", Wiley & Sons, 1985, pp. 180, 181.

Roffey, "Photopolymerization of Surface Coatings", Wiley & Sons, 1982, pp. 70, 71, 76, 77, 78, 88–89.

Weinberg, "Techniques of Chemistry", vol. V, Part 1, "Technique of Electroorganic Synthesis", Wiley & Sons, 1974, pp. 438, 519.-

INKS CONTAINING A TERNARY PHOTOINITIATOR SYSTEM AND IMAGE GRAPHICS PREPARED USING SAME

This is a continuation of application Ser. No. 08/695,566 filed Aug. 12, 1996 now abandoned, which is continuation of prior application Ser. No. 08/365,494, filed on Dec. 28, 1994, now U.S. Pat. No. 5,545,676, which was a continuation of prior application Ser. No. 07/840,880, filed on Feb. 25, 1992, abandoned, which was a continuation of prior application Ser. No. 07/034,065, filed on Apr. 2, 1987, abandoned.

TECHNICAL FIELD

This invention relates to photoinitiator systems for use in addition (free radically-initiated) polymerization.

BACKGROUND ART

Aryliodonium salts have been previously described for use as photoinitiators in addition-polymerizable compositions. References relating to such compositions include U.S. Pat. Nos. 3,729,313, 3,741,769, 3,808,006, 4,2281,232, 4,250,053 and 4,428,807; H. J. Timpe and H. Baumann, *Wiss. Z. Tech. Hochsch. Leuna-Merseburg*, 26, 439 (1984); H. Baumann, B. Strehmel, H. J. Timpe and U. Lammel, *J. Prakt. Chem*, 326 (3), 415 (1984); and H. Baumann, U. Oertel and H. J. Timpe, *Euro. Polym. J.*, 22 (4), 313 (Apr. 3, 1986).

Mono- and di-ketones have also previously been described for use as photoinitiators in addition-polymerizable compositions. References relating to such compositions include U.S. Pat. Nos. 3,427,161, 3,756,827, 3,759,807 and 4,071,424; U.K. Pat. Specification No. 1,304, 112; European Published Pat. Appl. No. 150,952 and *Chem. Abs.* 95:225704U.

SUMMARY OF THE INVENTION

The present invention provides, in one aspect, an addition-polymerizable composition comprising:
a) free-radically-polymerizable monomer ("monomer"), and
b) photoinitiator system, soluble in said monomer, comprising photochemically effective amounts of
  i) diaryliodonium salt "iodonium salt"),
  ii) sensitizing compound ("sensitizer") capable of absorbing light somewhere within the range of wavelengths between about 300 and about 1000 nanometers and capable of sensitizing 2-methyl-4,6-bi (trichloromethyl)-s-triazine, and
  iii) electron donor compound ("donor"),
said donor being different from said sensitizer and wherein zero$<E_{ox}$ (donor)$\leq E_{ox}$ (p-dimethoxybenzene).

The compositions of the invention provide a very useful combination of cure speed, cure depth and shelf life. They cure well even when loaded with large amounts of fillers, and can be used in a variety of applications including graphic arts imaging (e.g., for color proofing systems, curable inks, or silverless imaging), printing plates (e.g., projection plates or laser plates), photoresists, solder masks, coated abrasives, magnetic media, photocurable adhesives (e.g., for orthodontics) and photocurable composites (e.g., for antibody repair or dentistry).

The invention also provides a method for preparing photopolymerized compositions, and polymerized articles made therefrom.

DETAILED DESCRIPTION OF THE INVENTION

A wide variety of monomers can be photopolymerized using the photoinitiator system of the invention. Suitable monomers contain at least one ethylenically-unsaturated double bond, can be oligomers, and are capable of undergoing addition polymerization. Such monomers include mono-, di- or poly- acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyldimethylmethane, bis[1-(3-acryloxy-2-hydroxy)]-p-propoxyphenyldimethylmethane, trishydroxyethyl-isocyanurate trimethacrylate; the bis-acrylates and bis-methacrylates of polyethylene glycols of molecular weight 200–500, copolymerizable mixtures of acrylated monomers such as those of U.S. Pat. No. 4,652, 274, and acrylated oligomers such as those of U.S. Pat. No. 4,642,126; unsaturated asides such as methylene bis-acrylamide, methylene bis-methacrylamide, 1,6-hexamethylene bis-acrylamide, diethylene triamine tris-acrylamide and beta-methacrylaminoethyl methacrylate; and vinyl compounds such as styrene, diallyl phthalate, divinyl succinate, divinyl adipate and divinylphthalate. Mixtures of two or more monomers can be used if desired.

The monomer is combined with a three component or ternary photoinitiator system. The first component in the photoinitiator system is the iodonium salt, i.e., a diaryliodonium salt. The iodonium salt should be soluble in the monomer and preferably is shelf-stable (i.e., does not spontaneously promote polymerization) when dissolved therein in the presence of the sensitizer and donor. Accordingly, selection of a particular iodonium salt may depend to some extent upon the particular monomer, sensitizer and donor chosen. Suitable iodonium salts are described in U.S. Pat. Nos. 3,729,313, 3,741,769, 3,808,006, 4,250.053 and 4,394, 403, the iodonium salt disclosures of which are incorporated herein by reference. The iodonium salt can be a simple salt (e.g., containing an anion such as $Cl^-$, $Br^-$, $I^-$ or $C_4H_5SO_3^-$) or a metal complex salt (e.g., containing an anion such as $BR_4^-$, $PF_6^-$, $SbFr_6^-$, $SbF_5OH^-$ or $AsF_6^-$). Mixtures of iodonium salts can be used if desired.

Preferred iodonium salts include diphenyliodonium salts such as diphenyliodonium chloride, diphenyliodonium hexafluorophosphate and diphenyliodonium tetrafluoroborate.

The second component in the photoinitiator system is the sensitizer. The sensitizer should be soluble in the monomer, and is capable of light absorption somewhere within the range of wavelengths between about 300 and about 1000 nanometers, more preferably about 400 and about 700 nanometers and most preferably about 400 to about 600 nanometers. The sensitizer is also capable of sensitizing 2-methyl-4,6-bis(trichloromethyl)-s-triazine, using the test procedure described in U.S. Pat. No. 3,729,313. Using currently available materials, that test is carried out as follows. A standard test solution is prepared having the following composition:

5.0 parts of a 5% (weight by volume) solution in methanol of 45,000–55,000 molecular weight, 9.0–13.0% hydroxyl content polyvinyl butyral ("Butvar B76", Monsanto)

0.3 parts trimethylolpropone trimethacrylate 0.03 parts 2-methyl-4,6-bis(trichloromethyl)-s-triazine (see *Bull. Chem. Soc. Japan,* 42, 2924–2930, 1969).

To this solution is added 0.01 parts of the compound to be tested as a sensitizer. The solution is knife-coated onto a 0.05 mm clear polyester film using a knife orifice of 0.05 mm, and the coating is air dried for about 30 minutes. A 0.05 mm clear polyester cover film is carefully placed over the dried but soft and tacky coating with minimum entrapment of air. The resulting sandwich construction is then exposed for three minutes to 161,000 Lux of incident light from a tungsten light source providing light in both the visible and ultraviolet range ("FCH" 650 watt quartz-iodine lamp, General Electric).

Exposure is made through a stencil so as to provide exposed and unexposed areas in the construction. After exposure the cover film is removed and the coating is treated with a finely divided colored powder, such as a color toner powder of the type conventionally used in xerography. If the tested compound is a sensitizer, the trimethylolpropane trimethacrylate monomer will be polymerized in the light-exposed areas by the light-generated free radicals from the 2-methyl-4,6-bis(trichloromethyl)-s-triazine. Since the polymerized areas will be essentially tack-free, the colored powder will selectively adhere only to the tacky, unexposed areas of the coating, providing a visual image corresponding to that in the stencil.

Preferably, in addition to passing the above test, a sensitizer is also selected based in part upon shelf stability considerations. Accordingly, selection of a particular sensitizer may depend to some extent upon the particular monomer, iodonium salt and donor chosen.

Suitable sensitizers are believed to include compounds in the following categories: ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes and pyridinium dyes. Ketones (e.g., monoketones or alpha-diketones), ketocoumarins, aminoarylketones and p-substituted aminostyryl ketone compounds are preferred sensitizers. For applications requiring high sensitivity (e.g., graphic arts), it is preferred to employ a sensitizer containing a julolidinyl moiety. For applications requiring deep cure (e.g., cure of highly-filled composites), it is preferred to employ sensitizers having an extinction coefficient below about 1000, more preferably below about 100, at the desired wavelength of irradiation for photopolymerization.

By way of example, a preferred class of ketone sensitizers has the formula;

ACO(X)$_b$B where X is CO or CR$^1$R$^2$, where R$^1$ and R$^2$ can be the same or different, and can be hydrogen, alkyl, alkaryl or aralkyl, b is zero or 1, and A and B can be the same or different and can be substituted (having one or more non-interfering substituents) or unsubstituted aryl, alkyl, alkaryl, or aralkyl groups, or together A and B can form a cyclic structure which can be a substituted or unsubstituted cycloaliphatic, aromatic, heteroaromatic or fused aromatic ring.

Suitable ketones of the above formula include monoketones (b=0) such as 2,2-, 4,4- or 2,4-dihydroxy-benzophenone, di-2-pyridyl ketone, di-2-furanyl ketone, di-2-thiophenyl ketone, benzoin, fluorenone, chalcone, Michler's ketone, 2-fluoro-9-fluorenone, 2-chlorothioxanthone, acetophenone, benzophenone, 1- or 2-acetonaphthone, 9-acetylanthracene, 2-, 3- or 9-acetylphenanthrene, 4-acetylbiphenyl, propiophenone, n-butyrophenone, valerophenone, 2-, 3- or 4-acetylpyridine, 3-acetylcoumarin and the like. Suitable diketones include aralkyldiketones such as anthraquinone, phenanthrenequinone, o-, m- and p-diacetylbenzene, 1,3-, 1,4-, 1,5-, 1,6-, 1,7- and 1,8-diacetylnaphthalene, 1,5-, 1,8- and 9,10-diacerylanthracene, and the like. Suitable α-diketones (b=1 and x=CO) include 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'-, 3,3'- and 4,4'-dihydroxylbenzil, furil, di-3,3'-indolylethanedione, 2,3-bornanedione (camphorquinone), biacetyl, 1,2-cyclohexanedione, 1,2-naphthaquinone, acenaphthaquinone, and the like.

Preferred ketocoumarins and p-substituted aminostyryl ketone compounds are listed in TABLE II, below.

The third component in the photoinitiator system is the electron donor. A wide variety of donors can be employed. The donor is soluble in the monomer, and should meet the oxidation potential (E$_{ox}$) limitation discussed in more detail below. Preferably, the donor also is selected based in part upon shelf stability considerations. Accordingly, selection of a particular donor may depend in part on the monomer, iodonium salt and sensitizer chosen. Suitable donors are capable of increasing the speed of cure or depth of cure of a composition or the invention upon exposure to light of the desired wavelength. Also, the donor has an E$_{ox}$ greater than zero and less than or equal to E$_{ox}$(p-dimethoxybenzene). Preferably E$_{ox}$ (donor) is between about 0.5 and 1 volts vs. a saturated calomel electrode "S.C.E."). E$_{ox}$ (donor) values can be measured experimentally, or obtained from references such a; N. L. Weinburg, Ed., *Technique of Electroorganic Synthesis Part II Techniques of Chemistry*, Vol. V (1975), and C. R. Mann and K. K. Barnes, *Electrochemical Reactions in Nonagueous Systems* (1970).

Preferred donors include amines (including aminoaldehydes and aminosilanes), amides (including phosphoramides), ethers (including thioethers), ureas (including thioureas), ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenyl-boronic acid. The donor can be unsubstituted or substituted with one or more non-interfering substituents. Particularly preferred donors contain an electron donor atom such as a nitrogen, oxygen, phosphorus, or sulfur atom, and an abstractable hydrogen atom bonded to a carbon or silicon atom alpha to the electron donor atom.

Preferred amine donor compounds include alkyl-, aryl-, alkaryl- and aralkyl-amines such as methylamine, ethylamine, propylamine, butylamine, triethanolamine, amylamine, hexylamine, 2,4-dimethylaniline, 2,3-dimethylaniline, o-, m- and p-toluidine, benzylamine, aminopyridine, N,N'-dimethylethylenediamine, N,N'-diethylethylenediamine, N,N'-dibenzylethylonediamine, N,N'-diethyl-1,3-propanediamine, N,N'-diethyl-2-butene-1, 4-diamine, N,N'-dimethyl-1,6-hexanediamine, piperazine, 4,4'-trimethylenedipiperidine, 4,4'-ethylenedipiperidine, p-N,N-dimethylaminophenethanol and p-N,N-dimethylaminobenzonittile, aminoaldehydes such as p-N,N-dimethylaminobenzaldehyde, p-N,N-diethylaminobenzaldehyde, 9-julolidine carboxaldehyde and 4-morpholinobenzaldehyde, and aminosilanes such as trimethylsilylmorpholine, trimethylsllylpiperldine, bis (dimethylamino)diphenylsilane, tris(dimethylamino) methylsilane, N,N-diethylaminotrimethylsilane, tris (dimethylamino)phenyisilane, tris(methylsilyl)amine, tris (dimethylsilyl)amine, bis(dimethylsilyl)amine, N,N-bis (dimethylsilyl)aniline, N-phenyl-N-dimethylsilylaniline and N,N-dimtthyl-N-dimethylsilylamine. Tertiary aromatic alkylamines, particularly those having at least one electron-withdrawing group on the aromatic ring, have is been found to provide especially good shelf stability. Good shelf stability has also been obtained using amines that are solids at room temperature. Good photographic speed has been obtained using amines that contain one or more julolidinyl moieties.

Preferred amide donor compounds include N,N-dimethylacetamide, N,N-diethylacetamide, N-mothyl-N-phenylacetamide, hexamethylphosphoramide, hexaethylphosphoramide, hexapropylphosphoramide, trimorpholinophosphine oxide and tripiperidinophosphine oxide.

Suitable ether donor compounds include 4,4'-dimethoxybiphenyl, 1,2,4-trimethoxybenzene and 1,2,4,5-tetramethoxybenzene.

Suitable urea donor compounds include N,N'-dimethylurea, N,N-dimethylurea, N,N'-diphenylurea, tetramethylthiourea, tetraethylthiourea, tetra-n-butylthiourea, N,N-di-n-butylthiourea, N,N'-di-n-butylthiouren, N,N-diphenylthiourea and N,N'-diphenyl-N,N'-diethylthiourea.

The three components of the photoinitiator system are present in "photochemically effective amounts", that is, amounts of each component sufficient to enable the monomer to undergo photochemical gelation or hardening upon exposure to light of the desired wavelength. Preferably, for every 100 parts of monomer, a composition of the invention contains about 0.005 to about 10 parts (more preferably about 0.1 to about 4 parts) each of iodonium salt, sensitizer and donor. The amounts of each component are independently variable and thus need not be equal, with larger amounts generally providing faster cure, but shorter shelf life. Sensitizers with high extinction coefficients (e.g., above about 10,000) at the desired wavelength of irradiation for photopolymerization generally are used in reduced amounts.

The compositions of the invention can contain a wide variety of adjuvants depending upon the desired end use. Suitable adjuvants include solvents, diluents, resins, binders, plasticizers, pigments, dyes, inorganic or organic reinforcing or extending fillers (at preferred amounts of about 10% to about 90% by weight, based on the total weight of the composition), thixotropic agents, indicators, inhibitors, stabilizers, UV absorbers, medicaments (e.g., leachable fluorides) and the like. The amounts and types of such adjuvants, and their manner of addition to a composition of the invention will be familiar to those skilled in the art.

The compositions of the invention can be cured using a variety of methods. It is convenient to employ light sources that emit ultraviolet or visible light such as quartz halogen lamps, tungsten-halogen lamps, mercury arcs, carbon arcs, low-, medium-, and high-pressure mercury lamps, plasma arcs, light emitting diodes and lasers. Electron beam ("E-beam") irradiation and other curing devices that do not depend on light emission can also be employed. In general, heat or an inert atmosphere will accelerate cure.

The following examples are offered to aid in understanding the invention and are not to be construed as limiting the scope thereof. Unless otherwise indicated, all parts and percentages are by weight.

EXAMPLE 1

Three stock solutions were prepared from 0.25 parts camphorquinone (CPQ), 50 parts triethyleneglycol dimethacrylate (TEGDMA) and 50 parts bisphenol A diglycidyl ether dimethacrylate (BisGMA). 0.50 Part diphenyliodonium hexafluorophosphate ($\phi_2 I^+ PF_6^-$) was added to the first solution. 0.25 Part sodium p-toluenesulfinate (STS) was added to the second solution. 0.50 Part $\phi_2 I^+ PF_6^-$ and 0.25 part STS were added to the third solution. Each solution was poured into a 6 mm diameter "Teflon" mold to a depth of 2.5 mm, covered with polyester film and irradiated for 10 seconds using a handheld visible light curing lamp ("Visilux", 3M) whose lightguide output end was placed directly on the polyester film.

The solutions containing only CPQ and $\phi_2 I^+ PF_6^-$ or CPQ and STS formed a soft gel. The solution containing CPS, $\phi_2 I^+ PF_6^-$ and STS hardened to a solid having a Barcol hardness of 40 (ASTM D-2583) on both its top and bottom surfaces.

In a further experiment, three stock solutions were prepared from 11.85 parts each of the above monomers, 76 parts filler, and 0.25 part CPQ. 0.25 Part $\phi_2 I^+ PF_6^-$ was added to the first solution. 0.25 Part N,N-dimethylaminophenethyl alcohol ("D-1") was added to the second solution. 0.25 Part $\phi_2 I^+ PF_6^-$ and 0.25 part D-1 were added to the third solution. Each solution was cured in a mold as described above, but using a 6 mm deep mold and a 20 second cure time. The solution containing only $\phi_2 I^+ PF_6^-$ did not cure. The solution containing only D-1 had top and bottom Barcol hardness values of 56 and 2, respectively. The solution containing both $\phi_2 I^+ PF_6^-$ and D-1 had top and bottom Barcol hardness values of 60 and 30, respectively.

The above data illustrates that an increased degree of polymerization and depth of cure can be obtained using a composition of the invention.

EXAMPLE 2

Equimolar amounts of a variety of donors were added to monomer stock solutions containing 50 parts trimethylolpropane trimethacrylate, 50 parts 1,4-butanediol dimethacrylate, 0.25 part CPQ and optionally 0.5 part of the iodonium salt $\phi_2 I^+ PF_6^-$.

The resulting solutions were irradiated with visible light at an intensity of 60 mw/cm$^2$ (as measured by a United Detector Technology Model 351 portable photometer/radiometer) at 400–500 nm. The solutions were stirred using a glass rod and the time required to reach the gelation point was recorded. Set out below in TABLE I are the run number, donor compound, $E_{ox}$ (donor), weight percent donor, and gel times for solutions prepared with and without the iodonium salt. The donors are listed in TABLE I in order of generally decreasing oxidation potential.

TABLE I

| | | | | Gel time, seconds | |
| --- | --- | --- | --- | --- | --- |
| Run No. | Donor | $E_{ox}$ (donor) | % donor | Sensitizer/ donor | Sensitizer/ donor/ iodonium salt |
| 1 | control | | 0 | >200 | 190 |
| 2 | acetonitrile | 2.60 | 0.124 | >200 | >190 |
| 3 | nitrobenzene | | 0.373 | >200 | >190 |
| 4 | methylethylketone | | 0.218 | >200 | >190 |
| 5 | 2,5-dimethyl-2,4-hexadiene | 2.10 | 0.334 | >200 | >190 |
| 6 | ethylmethylthioacetate | 1.70 | 0.407 | >200 | >190 |
| 7 | p-bromothioanisole | 1.60 | 0.615 | >200 | >190 |
| 8 | 3,3'-dimethoxybiphenyl | 1.60 | 0.649 | >200 | >190 |
| 9 | tetrahydrofuran | 1.60 | 0.220 | >200 | >190 |
| 10 | hexaethylbenzene | 1.49 | 0.492 | >200 | >190 |
| 11 | methoxyphenylphenylether | | 0.604 | >200 | 188 |
| 12 | p-dimethoxybenzene | 1.34 | 0.418 | 205 | 160 |
| 13 | N,N-dimethylacetamide | 1.32 | 0.264 | 204 | 150 |
| 14 | phenylacetate | 1.30 | 0.413 | >200 | >190 |
| 15 | n-propylamine | 1.30 | 0.200 | 90 | 24 |
| 16 | aniline | 1.28 | 0.282 | >200 | >190 |
| 17 | 1,3-dibutylthiourea | | 0.570 | >200 | 137 |
| 18 | tetramethylurea | | 0.352 | 94 | 101 |
| 19 | tetrabutylthiourea | | 0.909 | 38 | 29 |

TABLE I-continued

| Run No. | Donor | $E_{ox}$ (donor) | % donor | Gel time, seconds Sensitizer/ donor | Sensitizer/ donor/ iodonium salt |
|---|---|---|---|---|---|
| 20 | dipentylamine | 1.22 | 0.477 | 159 | 19 |
| 21 | 1,2,4-trimethoxybenzene | 1.12 | 0.509 | >225 | 55 |
| 22 | hexamethyl-phosphoramide | 1.00 | 0.543 | 80 | 50 |
| 23 | tripiperdinophosphine oxide | 1.00 | 0.907 | 52 | 40 |
| 24 | trimethylsilylmorpholine | | 0.483 | 112 | 21 |
| 25 | N,N-dimethylbenzyl-amine | 1.00 | 0.410 | 18 | 8 |
| 26 | tris-dimethylsilylamine | | 0.580 | 108 | 32 |
| 27 | triethanolamine | 0.96 | 0.452 | 17 | 6 |
| 28 | tris(dimethylamino)-phenylsilane | | 0.719 | 15 | 9 |
| 29 | triphenylamine | 0.86 | 0.737 | >200 | >190 |
| 30 | triphenylphosphine | | 0.794 | >200 | 172 |
| 31 | p-dimethylamino-benzaldehyde | 0.70 | 0.452 | 13 | 11 |
| 32 | N,N-dimethyl-p-toluidine | 0.65 | 0.410 | 14 | 7 |
| 33 | p-dimethylaminophenyl alcohol | 0.65 | 0.500 | 13 | 8 |

The above data illustrates that an increased cure rate is obtained using a composition of the invention, and demonstrates the advantage or using donors whose $E_{ox}$ value is less than or equal to that of p-dimethoxybenzene and that have an abstractable hydrogen atom on a carbon or silicon atom alpha to the donor atom.

EXAMPLE 3

Solutions similar to those of U.S. Pat. No. 4,228,232 (Rousseau) were prepared from 4.3 parts pentaerythritol tetraacrylate, 5.6 parts "Oligomer P-II" (Rousseau, Col. 11, 61% by weight in MEK), 0.30 parts triethylamine, 14.9 parts of a dispersion containing 4.1% Pigment Red 48 (CI 15865) and 8.2% polyvinyl formal resin ("Formvar 12/85", Monsanto) in n-propanol-water azeotrope, and 74.2 parts n-propanol-water azeotrope. As was tile case in Rousseau, the amount of triethylamine was just sufficient to neutralize the acid in oligomer P-II, and thus the triethylamine did not serve as a donor. To 5 parts of the above solutions wore added 0.02 part $\phi_2 I^+ PF_6^-$, varying amounts of various sensitizers, and optionally 0.015 part of the donor compound 9-julolidline carboxyaldehyde. The solutions were then coated with wire-wound rods onto grained and anodized aluminum at coating weight of 1–2 g/m² and dried at 66° C. for 2 minutes. The resulting photosensitive printing plates were topcoated with 5% aqueous polyvinyl alcohol containing 0.26 parts surfactant ("Triton X-100", Rohm and Haas) as a coating aid at coating weights of 1–2 g/m². The dried plates were exposed through a $\sqrt{2}$ density increment, 21 step sensitivity guide (Stouffer Graphic Arts) for 2 sec. using a 172,000 Lux tungsten light source at a distance of 25.4 cm ("Model 70" Transparency Maker, 3M). The exposed plates were developed with an aqueous solution of 4% n-propanol, 2% sodium metasilicate and 0.06% surfactant ("Dowfax 2AL". Dow Chemical Company). Set out below in TABLE II are the run number, the type and amount of sensitizer and its $\lambda_{max}$ value, a statement ( "yes" or "no") indicating whether or not the optional donor was added, and the number of solid steps retained after exposure and development. Higher step values indicate greater sensitivity. Exposure values (in ergs/cm² required to form one solid step; last column in TABLE II) for many of the plates were also measured by exposing the plates to coherent light using an argon-ion laser (488 nm), or by exposing the plates to incoherent light at the absorption maximum of the sensitizer using a one Kw high pressure mercury-xenon light source directed through a variable frequency monochromator having a 20 nm bandpass. The monochromator output was measured using a radiometer. Numerically lower exposure values indicate increased sensitivity.

From the data in TABLE II it can be seen that plates containing iodonium salt, sensitizer and donor are more sensitive than plates containing only iodonium salt and sensitizer. An exposure value of 450 ergs/cm² at 488 nm (argon-ion laser) was obtained using a combination of diphenyliodonium salt, ketocoumarin sensitizer, and 9-julolidine carboxaldehyde (Run 8). For comparison, the relatively sensitive laser-imageable compositions of Rousseau Exs. 18 and 19 (cols. 18–19) have an exposure value at 488 nm of only 3,200 ergs/m².

TABLE II

| Run No. | Sensitizer Type | Amount | $\lambda_{max}$, nm | Add'l donor | Solid steps[a] | Sensitivity ergs/cm², (wavelength) |
|---|---|---|---|---|---|---|
| 1 | 3-(p-dimethyl-aminocinnamoyl)-7-dimethyl-aminocoumarin | 0.005 | 475 | no | 10 | 10,000[b] (488 nm) |
| 2 | 3-(p-dimethyl-aminocinnamoyl)-7-dimethyl-aminocoumarin | " | " | yes | 13 | 3,000[b] (488 nm) |
| 3 | 3-(p-diethyl-aminocinnamoyl)-7-dimethyl-aminocoumarin | 0.005 | 480 | no | 13 | 3,000[b] (488 nm) |
| 4 | 3-(p-diethyl-aminocinnamoyl)-7-dimethyl-aminocoumarin | " | " | yes | 15 | 900[b] (488 nm) |
| 5 | 9'-julolidine-4-piperidino-acetophenone | 0.008 | 450 | no | 15 | 900 (450 nm) |
| 6 | 9'-julolidine-4-piperidino-acetophenone | " | " | yes | 18 | 300 (450 nm) |
| 7 | 9-(4-diethyl-aminocinnamoyl)-1,2,4,5-tetrahydro-3H,6H,10H[1]benzopyrano[6,7,8-i,j]quinolizine-10-one | 0.005 | 500 | no | 14 | 1,400[b] (488 nm) |
| 8 | 9-(4-diethyl-aminocinnamoyl)-1,2,4,5-tetrahydro-3H,6H,10H[1]benzopyrano[6,7,8-i,j]quinolizine-10-one | " | " | yes | 16 | 450[b] (488 nm) |
| 9 | 9-(4-dicyano-ethylamino-cinnamoyl)-1,2,4,5-tetrahydro-3H,6H,10H[1]benzo-pyrano[6,7,8-i,j]-quinolazine-10-one | 0.005 | 495 | no | 8 | [c] |
| 10 | 9-(4-dicyano-ethylamino-cinnamoyl)-1,2,4,5-tetrahydro-3H,6H,10H[1]benzo-pyrano[6,7,8-i,j]-quinolazine-10- | " | " | yes | 12 | [c] |

TABLE II-continued

| Run No. | Sensitizer Type | Amount | $\lambda_{max}$, nm | Add'l donor | Solid steps[a] | Sensitivity ergs/cm², (wavelength) |
|---|---|---|---|---|---|---|
| 11 | 2,3-bis(9'-julolidone)cyclopentanone | 0.005 | 525 | no | 12 | 3,200 (514 nm) |
| 12 | 2,3-bis(9'-julolidone)cyclopentanone | " | " | yes | 14 | 1,400 (514 nm) |
| 13 | 9-ethoxycarbonyl-1,2,4,5-tetrahydro-3H,6H,10H-[1]benzopyrano[6,7,8-i,j]quinolizine-10-one | 0.008 | 435 | no | 16 | 500 (435 nm) |
| 14 | 9-ethoxycarbonyl-1,2,4,5-tetrahydro-3H,6H,10H-[1]benzopyrano[6,7,8-i,j]quinolizine-10-one | " | " | yes | 18 | 250 (435 nm) |
| 15 | 2-(4'-diethylaminobenzylidine)-1-indanone | 0.008 | 439 | no | 12 | (c) |
| 16 | 2-(4'-diethylaminobenzylidine)-1-indanone | " | " | yes | 14 | (c) |
| 17 | 9-acetyl-1,2,4,5-tetrahydro-3H,6H,10H[1]benzopyrano[6,7,8-i,j]quinolizine-10-one | 0.008 | 450 | no | 13 | 3,200 (450 nm) |
| 18 | 9-acetyl-1,2,4,5-tetrahydro-3H,6H,10H[1]benzopyrano[6,7,8-i,j]quinolizine-10-one | " | " | yes | 15 | 1,500 (450 nm) |
| 19 | 5,10-diethoxy-12,16,17-trichloroviolanthrene | 0.005 | 540 | no | 3 | (c) |
| 20 | 5,10-diethoxy-12,16,17-trichloroviolanthrene | " | " | yes | 6 | (c) |

Notes to TABLE II:
" = Ditto
[a]Exposure using tungsten light source.
[b]Exposure using 488 nm argon-ion laser.
[c]Not determined.

EXAMPLE 4

A coating formulation was prepared from the following ingredients:

| | % Solids |
|---|---|
| acrylamide | 43.3 |
| N,N'-methylenebisacrylamide | 4.3 |
| polyvinyl alcohol (m.w. 2000, 75% hydrolyzed) | 51.9 |
| surfactant ("Triton X-100") | 0.5 | made up to 11.5% solids in a 1/1 v/v acetonitrile/water mixture. Using a red safelight, coating samples were prepared by combining 25 ml portions of the above stock solution with 0.01 g of the sensitizer and optionally adding 0.1 g ,$\Phi_2I^+PF_6^-$ and/or 0.1 g STS. The samples were coated onto gelatin-subbed polyester film using a #18 wire wound rod, dried with a heat gun, then oven-dried for 2 minutes at 60° C. The coated films were exposed under vacuum through a 21 step sensitivity guide, using a tungsten ("Model 70" Transparency Maker, 3M) or ultraviolet (2 Kw Berkey Ascor, Berkey Technical Company) light source. The exposed samples were developed using a 3/20, v/v water/methanol solvent mixture. Relative speed was determined by the number of steps (average of 3 samples) remaining after development. Set out below in TABLE III are the results for the samples exposed to visible light, and set out below in TABLE IV are the results for the samples exposed to ultraviolet light. Each exposure was 30 sec. in the visible region or 60 sec. in the ultraviolet region except as noted.

TABLE III

Visible Light Sensitivity Enhancement

| | | | Solid steps | | |
|---|---|---|---|---|---|
| Run No. | Sensitizer | Sensitizer $\lambda_{max}$, nm | Sensitizer/ donor | Sensitizer/ iodonium salt | Sensitizer/ donor/ iodonium salt |
| 1 | methylene blue | 661 | (c) | 3 | 12 |
| 2 | toluidine blue | 626 | 6 | (c) | 16 |
| 3 | rose bengal | 548 | (d) | (c) | 16 |
| 4 | phenosafranine | 520 | (d) | (c) | 9 |
| 5 | 1,3-bis(4-dimethyl-aminobenzil-idene)acetone[a] | 434 | (d) | 11 | 17 |
| 6 | tris(bipyridyl)ruthenium(+2) chloride | 453 | (d) | (c) | 12 |
| 7 | crystal violet[b] | 593 | (d) | (c) | 10 |
| 8 | eosin yellow | 517 | (c) | 4 | 12 |
| 9 | 3,3'-dimethylthiocarbocyanine iodide[a] | 553 | (d) | (c) | 12 |

Notes to TABLE III:
[a]5 sec. exposure.
[b]60 sec. exposure.
[c]Image lost during development.
[d]No image formed.

TABLE IV

Ultraviolet Light Sensitivity Enhancement

| | | | Solid steps | | |
|---|---|---|---|---|---|
| Run No. | Sensitizer | Sensitizer $\lambda_{max}$, nm | Sensitizer/ donor | Sensitizer/ iodonium salt | Sensitizer/ donor/ iodonium salt |
| 1 | 2,5-bis(cinamylidene)cyclopentanone | 400 | (b) | (b) | 8 |
| 2 | 4'-methoxybenzylidene-4-nitro-acetophenone | 356 | (b) | (b) | 11 |
| 3 | 2-(4-dimethylaminobenzilidene)-dimethylmalonate | 377 | (b) | (c) | 5 |
| 4 | Michler's ketone[a] | 355 | (b) | 10 | 15 |
| 5 | 2-chlorothioxanthone | 387 | (b) | (c) | 11 |

Notes to TABLE IV:
[a]15 Second exposure at 40% power.
[b]No image formed.
[c]Image lost during development.

The above data illustrates that combination of an iodonium salt, sensitizer and donor can increase imaging speed by one to two orders of magnitude compared to compositions containing only sensitizer and donor or only sensitizer and iodonium salt.

EXAMPLE 5

To illustrate the effect of $E_{ox}$ (donor) upon cure speed, a series of compositions was evaluated as follows. A monomer stock solution was prepared from 10% pentaerythritol tetraacrylate in 4/1, w/w, acetonitrile/water. To 3 ml portions of this solution in 13×10 mm "Pyrex" test tubes were added about 0.02 g of $\phi_2I^+PF_6^-$ and/or a donor compound and enough sensitizer to give an optical density of between 1 and 2, as evaluated visually. The solutions were purged with N, for 2 minutes before and continuously during light irradiation. The light source was a Kodak "Carousel" Projector lamp equipped with a 440 nm filter. Relative speed was determined by measuring Relation time.

Set out below in TABLE V are the run number, the sensitizers and their $\lambda_{max}$ values, the donor compounds and their $E_{ox}$ values, and the gelation times for solutions containing iodonium salt plus sensitizer, sensitizer plus donor, or iodonium salt plus sensitizer plus donor.

The resin-impregnated backing was knife-coated with the binder resin at a coating thickness of 0.1 mm, then drop-coated with grade 50 $Al_2O_3$ mineral. The binder was cured under nitrogen in 5 to 10 seconds using a high intensity visible light source (model F440 with 4v678 lamp, Fusion Systems) operated at a distance of about 15 cm. Microscopic examination of the cured abrasive showed that cure took place throughout the binder, even underneath individual mineral granules. By comparison, if the photoinitiator system was excluded from the resin and a 5Mrad dose of E-beam irradiation (250 Kv acceleration potential) was employed to effect cure, pools of wet uncured resin remained under individual mineral granules and the granules were poorly adhered on the backing.

A sample of the coated abrasive was size coated with the same resin system, using a coating weight just sufficient to coat the mineral granules. The size coat was cured under the visible light source used to cure the make coat. The resulting

TABLE V

| Run No. | Sensitizer Identity | $\lambda_{max}$ | Donor[a] | Gel time, sec. Iodonium salt/ sensitizer | Sensitizer/ Donor | Iodonium salt/ sensitizer/ donor |
|---|---|---|---|---|---|---|
| 1 | methylene blue | 661 | STS | [b] | [b] | 10 |
| 2 | thionin | 598 | STS | [b] | [b] | 180 |
| 3 | " | " | FC | [c] | [c] | <5 |
| 4 | phenosafrine | 520 | STS | [b] | [b] | 15 |
| 5 | rose bengal | 548 | STS | [b] | 30 | <5 |
| 6 | fluorescein | 491 | STS | [b] | [b] | 15 |
| 7 | crystal violet | 588 | STS | [b] | [b] | >300 |
| 8 | " | " | FC | [c] | [c] | 120 |
| 9 | malachite green | 614 | STS | [b] | [b] | >300 |
| 10 | " | " | FC | [c] | [c] | 60 |
| 11 | 3,3'-dimethylthiocarbocyanine iodide | 553 | STS | 60 | [b] | 30 |
| 12 | 2,6-bis(4-dimethylaminostyryl)-1-methyl-pyridinium iodide | 490 | STS | [b] | [b] | [b] |
| 13 | 2,6-bis(4-dimethylaminostyryl)-1-methyl-pyridinium iodide | " | FC | c) | [c] | 90 |
| 14 | tris(bipyridyl)ruthenium(+2) chloride | 453 | STS | 60 | 60 | <10 |
| 15 | 1-methylaminoanthraquinone | 502 | STS | [b] | [b] | 45 |
| 16 | 1,2,2-tricyano-1-(4-dimethylamino-phenyl)ethylene | 525 | STS | [b] | [b] | [b] |
| 17 | 1,2,2-tricyano-1-(4-dimethylamino-phenyl)ethylene | " | FC | [c] | [c] | 90 |

Notes to TABLE V:
[a]STS = sodium p-toluenesulfinate ($E_{ox}$ = 0.76); FC = ferrocyanide ($E_{ox}$ = 0.2).
[b]No reaction.
[c]Not determined.

The above data illustrates that when $E_{ox}$ (donor) is decreased, cure speed generally increases (see also TABLE I).

EXAMPLE 6

A polyester cloth backing (woven, spun polyester cloth, 0.03 g/cm², Milliken) was impregnated with resin by saturating the backing with an ultraviolet-light-curable resin mixture made by combining 75 parts epoxy-acrylate resin ("Novacure 3500", Interea), 15 parts pentaerythritol triacrylate, 9 parts n-vinyl pyrrolidone and 1 part α,α-dimethoxy-α-phenyl acetophenone, and curing the resin under ultraviolet light in air using an energy density of 0.3 J/cm².

A coated abrasive binder resin was prepared from a 50:50 mixture of the triacrylate of tris-hydroxyethyliso-cyanurae, and the triacrylate of trimethylolpropane, filled to 50% with calcium carbonite. 0.25 Part each of $\phi_2I^+PF_6^-$ CPQ and D-1 were mixed into the binder resin.

coated abrasive was evaluated using a reciprocating grinding apparatus ("rocker drum") on a 6 mm thick 1018 carbon steel workpiece. After 500 cycles, no shelling was observed and an average of 0.77 g of steel was removed. A comparison abrasive sample was prepared using a make coat that contained the same photoinitiator system (cured using visible light), and a size coat that did not contain the photoinitiator system (cured using E-beam). The comparison abrasive shelled after only 20 cycles and removed only 0.02 g of steel.

Comparable results were obtained when sensitizers such as benzil, 2-chlorothioxanthone and fluorenone were substituted for camphorquinone. Improved uncured resin shelf life and ambient light stability were obtained when donor compounds ouch as ethyl p-dimethylaminobenzoate, p-dimethylaminobenzaldehyde and p-dimethylaminobenzonitrile were substituted for p-dimethylaminophenethyl alcohol.

The above-described abrasive binder system should be a useful substitute for standard phenolic-based binders, and could offer reduced energy consumption and higher throughput during manufacture.

EXAMPLE 7

A visible-light-curable orthodontic bracket adhesive was prepared by mixing together 197 parts BisGMA, 197 parts TEGDMA, 1,618 parts silane-treated microparticles (Example 1, U.S. Pat. No. 4,503,169), 33 parts pyrogenic silica ("R-972", DeGussa), 2 parts $\phi_2I^+PF_6^-$, 1 part CPQ and 3 parts triethanolamine to yield a paste-like composition. A bovine incisal tooth was potted in a circular acrylic cylinder, and the labial surface of the tooth cleaned with a pumice slurry, rinsed, dried and etched with gelled 37% phosphoric arid for 1 minute. The tooth was rinsed with distilled water for 45 seconds, air dried, coated on its etched surface with a methacrylate-based primer ("Light-Curable Enamel Bond", 3M), blown with air to level the primer, and irradiated for 20 seconds with a handheld curing light ("visilux", 3M).

A thin film of the above-described orthodontic bracket adhesive was applied to the entire back surface of ( a standard stainless steel orthodontic bracket (4.0×4.0 mm, 100 mesh backing). The bracket was then pressed firmly against the etched, primed bovine tooth. The lightguide output end was oriented orthogonally with respect to the face of the bracket, at a distance of about 3 mm, and the light energized for 20 seconds.

Fifty brackets were bonded to teeth using the above procedure. The resulting cured bracket-tooth assemblies were stored for various periods of time, then clamped in the fixed jaw of an "Instron" tensile tester (Instron Engineering Corporation). The movable jaw of the tester was fastened to the bracket using a length of orthodontic wire. The shear force required to cause bond failure was measured at a jaw separation rate of 2 mm/minute, and an average value determined for five samples at each storage time. Set out below in TABLE VI are the storage times and measured average shear bond strengths for the above-described adhesive, along with comparison values for a conventional two-part chemical cure orthodontic adhesive ("Concise" No. 1960, 3M) and a commercially available one-part light cure orthodontic adhesive ("Heliosit", Vivadent, cured according to the manufacturer's instructions).

TABLE VI

| | Average shear bond strength, kg/cm² | | |
|---|---|---|---|
| Storage time | Adhesive of EXAMPLE 7 | Concise | Heliosit |
| 30 seconds | 103.3 | (c) | 53.6 |
| 2 minutes | 112.3 | (c) | 68.5 |
| 5 minutes | 102.9 | 82.0 | 77.2 |
| 10 minutes | 99.1 | 105.6 | 80.0 |
| 1 hour[a] | 142.9 | 150.0 | 86.1 |
| 24 hours[a][b] | 134.9 | 115.6 | 93.4 |
| 3 months[a] | 160.1 | (c) | (c) |
| 6 months[a] | 186.5 | (c) | (c) |
| 12 months[a] | 172.2 | (c) | (c) |
| 18 months[a] | 161.6 | (c) | (c) |

Notes to TABLE VI:
[a]Stored in 37° C. distilled water.
[b]Average of 10 samples, prepared using two different batches of adhesive.
[c]Not determined.

The commercial chemical cure adhesive requires at least 5 minutes waiting time before archwire application. The commercial light cure adhesive also requires some waiting time before archwire application, and its ultimate strength is believed to be insufficiently high to prevent occasional bracket adhesion failure. In contrast, the adhesive made from the photoinitiator system of this invention exhibits rapid strength buildup and high ultimate bond strength. It should enable immediate archwire application, and reduce the incidence of early bracket adhesion failure.

Various modifications and alterations of this invention will be apparent to those skilled in the art without departing from the scope and spirit Of this invention. It should be understood that this invention is not limited to the illustrative embodiments set forth herein.

We claim:
1. A curable ink, comprising:
   a photocurable addition-polymerizable composition comprising:
   a) free-radically-polymerizable monomer,
   b) photoinitiator system, soluble in said monomer, comprising photochemically effective amounts of
      i) aryliodonium salt,
      ii) sensitizing compound capable of absorbing light within the range of wavelengths between about 300 and about 1000 nanometers and capable of sensitizing 2-methyl-4,6-bis(trichloromethyl)-s-triazine, and
      iii) electron donor compound, said donor being different from said sensitizing compound wherein the oxidation potential of said donor is greater than zero and less than or equal to p-dimethoxybenzene vs. a saturated calomel electrode, and
   (c) pigment or dye or combinations thereof.
2. The curable ink according to claim 1, wherein the free-radically polymerizable monomer comprises a mixture of monomer and oligomer.
3. The curable ink according to claim 2, further comprising an adjuvant selected from the group consisting of solvents, diluents, resins, binders, plasticizers, indicators, inhibitors, stabilizers, UV absorbers, and combinations thereof.
4. The curable ink according to claim 1, wherein said range of wavelengths is about 400 to about 700 nanometers.
5. The curable ink according to claim 1, wherein said sensitizing compound is selected from the group consisting of ketones, coumarin dyes, xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines squarylium dyes and pyridinium dyes.
6. The curable ink according to claim 1, wherein said sensitizing compound comprises a ketone, ketocoumarin, aminoarylketone or p-substituted aminostyryl ketone compound.
7. The curable ink according to claim 1, wherein said sensitizing compound contains at least one julolidinyl moiety.
8. The curable ink according to claim 1, wherein said sensitizing compound comprises an α-diketone having an extinction coefficient below about 1000 at the wavelength at which said photocurable composition is irradiated when photopolymerized.
9. The curable ink according to claim 1, wherein said sensitizing compound comprises camphorquinone.
10. The curable ink according to claim 1, wherein said sensitizing compound has the formula:

where X is CO or $CR^1R^2$, where $R^1$ and $R^2$ are the same or different, and are hydrogen, alkyl, alkaryl or aralkyl, b is zero or 1, and A and B are the same or different and are substituted or unsubstituted aryl, alkyl, alkaryl or aralkyl groups, or together A and B form a cyclic structure which is a substituted or unsubstituted cycloaliphatic, aromatic, heteroaromatic or fused aromatic ring.

11. The curable ink according to claim 1 wherein said donor is selected from the group consisting of amines, amides, ethers, ureas, ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid.

12. The curable ink according to claim 1, wherein said donor contains a nitrogen, oxygen, phosphorus or sulfur donor atom and an abstractable hydrogen atom bonded to a carbon or silicon atom alpha to said donor atom.

13. The curable ink according to claim 1, wherein said donor comprises a tertiary amine containing an aromatic ring.

14. The curable ink according to claim 13, wherein there is at least one electron-withdrawing group on said aromatic ring.

15. The curable ink according to claim 1, wherein said donor contains one or more julolidinyl moieties.

16. The curable ink according to claim 15, wherein said donor comprises 9-julolidine carboxyaldehyde.

17. The curable ink according to claim 1, wherein said photocurable composition contains, for every 100 parts by weight of said monomer, about 0.005 to about 10 parts by weight each of said aryliodonium salt, said sensitizing compound and said donor.

18. An image graphic, comprising:
   a photocured image-bearing coating atop a support, wherein the coating is cured from an ink comprising a photocurable, addition-polymerizable composition comprising:
   a) free-radically-polymerizable monomer,
   b) photoinitiator system, soluble in said monomer, comprising photochemically effective amounts of
      i) aryliodonium salt,
      ii) sensitizing compound capable of absorbing light within the range of wavelengths between about 300 and about 1000 nanometers and capable of sensitizing 2-methyl-4,6-bis(trichloromethyl)-s-triazine, and
      iii) electron donor compound, said donor being, different from said sensitizing compound wherein the oxidation potential of said donor is greater than zero and less than or equal to p-dimethoxybenzene vs. a saturated calomel electrode, and
   c) pigment or ink or combinations thereof.

19. The image graphic according to claim 18, wherein the free-radically polymerizable monomer comprises a mixture of monomer and oligomer.

20. The image graphic according to claim 19, further comprising an adjuvant selected from the group consisting of solvents, diluents, resins, binders, plasticizers, indicators, inhibitors, stabilizers, UV absorbers, and combinations thereof.

21. The image graphic according to claim 18, wherein said range of wavelengths is about 400 to about 700 nanometers.

22. The image graphic according to claim 18, wherein said sensitizing compound is selected from the group consisting of ketones, coumarin dyes, xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines squarylium dyes and pyridinium dyes.

23. The image graphic according to claim 18, wherein said sensitizing compound comprises a ketone, ketocoumarin, aminoarylketone or p-substituted aminostyryl ketone compound.

24. The image graphic according to claim 18, wherein said sensitizing compound contains at least one julolidinyl moiety.

25. The image graphic according to claim 18, wherein said sensitizing compound comprises an α-diketone having an extinction coefficient below about 1000 at the wavelength at which said photocurable composition is irradiated when photopolymerized.

26. The image graphic according to claim 18, wherein said sensitizing compound comprises camphorquinone.

27. The image graphic according to claim 18, wherein said sensitizing compound has the formula:

ACO(X)$_b$B where X is CO or CR$^1$R$^2$, where R$^1$ and R$^2$ are the same or different, and are hydrogen, alkyl, alkaryl or aralkyl, b is zero or 1, and A and B are the same or different and are substituted or unsubstituted aryl, alkyl, alkaryl or aralkyl groups, or together A and B form a cyclic structure which is a substituted or unsubstituted cycloaliphatic, aromatic, heteroaromatic or fused aromatic ring.

28. The image graphic according claim 18 wherein said donor is selected from the group consisting of amines, amides, ethers, ureas, ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid.

29. The image graphic according to claim 18, wherein said donor contains a nitrogen, oxygen, phosphorus or sulfur donor atom and an abstractable hydrogen atom bonded to a carbon or silicon atom alpha to said donor atom.

30. The image graphic according to claim 18, wherein said donor comprises a tertiary amine containing an aromatic ring.

31. The image graphic according to claim 6, wherein there is at least one electron-withdrawing group on said aromatic ring.

32. The image graphic according to claim 18, wherein said donor contains one or more julolidinyl moieties.

33. The image graphic according to claim 32, wherein said donor comprises 9-julolidine carboxyaldehyde.

34. The image graphic according to claim 18, wherein said photocurable composition contains, for every 100 parts by weight of said monomer, about 0.005 to about 10 parts by weight each of said aryliodonium salt, said sensitizing compound and said donor.

35. A method for imaging graphics, comprising the steps of irradiating an ink including a composition with light having a wavelength between about 300 and about 1000 nanometers until said composition gels or hardens, said composition comprising:
   a) free-radically-polymerizable monomer,
   b) photoinitiator system, soluble in said monomer, comprising photochemically effective amounts of
      i) aryliodonium salt,
      ii) sensitizing compound capable of absorbing light somewhere within the range of wavelengths between about 300 and about 1000 nanometers and capable of sensitizing 2-methyl-4,6-bis(trichloromethyl)-s-triazine, and
      iii) electron donor compound, said donor being different from said sensitizing compound and wherein the oxidation potential of said donor is greater than zero vs. a saturated Calomel electrode, and
   c) pigment or dye or combinations thereof.

* * * * *